US012651648B2

(12) United States Patent
Lu et al.

(10) Patent No.: US 12,651,648 B2
(45) Date of Patent: Jun. 9, 2026

(54) UNIFIED PLATFORM FOR RAPID PRODUCTION OF NANOVACCINES WITH ENHANCED SAFETY, EFFICACY AND PRECISION

(71) Applicant: Santa Clara University, Santa Clara, CA (US)

(72) Inventors: Biao Lu, San Francisco, CA (US); Joy Ku, Sunnyvale, CA (US); Renceh Flojo, Pearl City, HI (US); Christopher James Olson, Menlo Park, CA (US)

(73) Assignee: Santa Clara University, Santa Clara, CA (US)

( * ) Notice: Subject to any disclaimer, the term of this patent is extended or adjusted under 35 U.S.C. 154(b) by 569 days.

(21) Appl. No.: 18/229,363

(22) Filed: Aug. 2, 2023

(65) Prior Publication Data

US 2024/0055079 A1 Feb. 15, 2024

Related U.S. Application Data

(60) Provisional application No. 63/397,477, filed on Aug. 12, 2022.

(51) Int. Cl.
| | |
|---|---|
| *A61K 39/00* | (2006.01) |
| *C12N 15/10* | (2006.01) |
| *G16B 40/20* | (2019.01) |

(52) U.S. Cl.
CPC .............. *G16B 40/20* (2019.02); *A61K 39/00* (2013.01); *C12N 15/1058* (2013.01); *A61K 2039/55555* (2013.01); *A61K 2039/645* (2013.01); *A61K 2039/70* (2013.01)

(58) Field of Classification Search
None
See application file for complete search history.

(56) References Cited

U.S. PATENT DOCUMENTS 7,981,601 B2 * 7/2011 Wang ..................... A61P 37/00
506/10

FOREIGN PATENT DOCUMENTS

KR 20210132323 A * 11/2021 .............. A61P 31/14

OTHER PUBLICATIONS

Naz et al., Designing Multi-Epitope Vaccines to Combat Emerging Coronavirus Disease 2019 (COVID-19) by Employing Immuno-Informatics Approach, Front Immunol. Jul. 10, 2020:11:1663. doi: 10.3389/fimmu.2020.01663. eCollection 2020.*
Jagadeb et al, Identification and evaluation of immunogenic MHC-I and MHC-II binding peptides from *Mycobacterium tuberculosis*, Comput Biol Med. Mar. 2021:130:104203. doi: 10.1016/j.compbiomed.2020.104203. Epub Dec. 29, 2020.*
Meyer et al, Pseudotyping exosomes for enhanced protein delivery in mammalian cells, International Journal of Nanomedicine. 2017; 12:3153-3170, DOI: 10.2147/ijn.s133430.*

* cited by examiner

*Primary Examiner* — Yung-Sheng M Tsui
(74) *Attorney, Agent, or Firm* — LUMEN PATENT FIRM

(57) ABSTRACT

A unified platform including an exosome-based method has been developed that uses only immunogenic epitopes for nanovaccine production. By eliminating these nonessential sequences from the full-length antigen, this new type of nanovaccine is safer as compared to those of existing vaccines. In addition, careful selection of targeting epitopes and incorporation of multiple epitope repeats into nanovaccine will make it more potent and precise than the traditional vaccines.

1 Claim, 10 Drawing Sheets

Traditional Vaccine extract      select antigen-independent, safe, precise cluster      repeat effective & potent Nanovaccine

FIG. 1C

Control exosome

Mean: 118.9+/- 0.5 nm

Mode: 71 +/- 0.2 nm

Nanovaccine

Mean: 104.3+/- 0.6 nm

Mode: 62 +/- 0.7 nm

Immunization

(antigen/epitope-displayed exosomes)

Week   0           4

→ End of study

Week 6

Sampling of

Blood & spleen cell response

- IgA levels
- IgG levels

T cell response

- Th1/Th2/Th9/Th17/Th22
- IL-1β, -2, 4, 5, 6, 9, 10, 12p70, 13, 17A, 18, 22, 23, 27, GM-CSF, IFN-r, TNF-α

UNIFIED PLATFORM FOR RAPID PRODUCTION OF NANOVACCINES WITH ENHANCED SAFETY, EFFICACY AND PRECISION

CROSS-REFERENCE TO RELATED APPLICATIONS

This application claims priority from U.S. Provisional Patent Application 63/397,477 filed Aug. 12, 2022, which is incorporated herein by reference.

FIELD OF THE INVENTION

This invention relates to an engineering strategy for rapid production of human cell-derived extracellular vesicle, or exosome-based vaccines with enhanced safety, efficacy and precision. In particular, the invention relates to a unified platform, which uses computational analysis and design, synthetic biology and surface display technology to stream-line the production of exosome-based nanovaccines in human 293T cells. This platform enables targeted presentation of small portion but highly immunogenic clusters selected from the full-length antigens, therefore ensuring efficacy, safety and specificity. Independent on nature of the full-length antigen sequences, this exosome-based nanovaccine can be used for the prevention and treatment of a broad range of human diseases, including but not limited to viral infections and human cancers.

BACKGROUND OF THE INVENTION

Vaccination has been one of the most effective public health interventions to prevent and treat infectious diseases and cancers. Vaccination has resulted in eradication of over 30 viral infections and effectively prevention of several human cancers. Despite these achievements, safety, efficacy and precision continue to be major hurdles that hinder rapid development of new vaccine to meet medical need. The development of a unified platform is a critical step in improving the new generation of vaccines. The objective of this invention is to develop a novel, unified and exosome-based platform for the rapid production of human cell-derived nanovaccine with enhanced safety, efficacy and precision. This type of vaccines will provide a better solution to the prevention and treatment of viral infections and cancers.

One of the major drawbacks of current vaccines is the use of whole pathogen or full-length antigen as vaccine components. The whole pathogen or full-length antigen contains not only immunological epitopes, essential for stimulating immune responses, but also non-essential sequences, which may cause toxicities and side effects to the host. Additionally, these non-essential sequences may also complicate vaccine design and production due to unexpected biological activities. The present invention addresses these problems.

SUMMARY OF THE INVENTION

A unified platform has been developed that uses only immunogenic epitopes for nanovaccine production. By eliminating these nonessential sequences from the full-length antigen, this new type of nanovaccine is safer as compared to those of existing vaccines. In addition, careful selection of targeting epitopes and incorporation of multiple epitope repeats into nanovaccine will make it more potent and precise than the traditional vaccines (FIGS. 1A-C).

A Novel and Complete Nano-Platform

Nanovaccines holds a great promise to enhance safety, efficacy and precision of the next generation of vaccines. Among various nanotechnologies, the recently discovered human cell-derived nanovesicles, termed as exosomes, exhibit outstanding properties that are superior over other nanomaterials including liposomes, polymers, and virus-like particles. By integrating three cutting-edge technologies, the inventors created an exosome-based platform, enabling a rapid production of safer and more effective nanovaccines for the prevention and treatment of human diseases.

These technologies include:

(1) an integrated bioinformatics software enables identification, retrieving, mapping and clustering of compounded epitopes within any full-length antigen;

(2) a strategy of selection, joining and synthesis of highly immunogenic clusters via synthetic biology and a sub-sequence fusion into an exosome-targeting scaffolds for expression vector constructions; and (3) a set of streamlined protocols to produce exosome-based nanovaccine via surface display technology using cultured human 293T cells.

An Integrated Software Enabling Simultaneous Analysis of all Classes of Epitopes Bioinformatics tools are imperative for high-throughput analysis of immunological epitopes embedded in sophisticated protein antigens. Existing software tools, however, aim to perform specific analysis for only a single class of epitopes, therefore limiting its usefulness in effective vaccine design. To solve this problem, the inventors have developed an integrated software that enables simultaneous searching of multiple online immunological databases and returning all classes of immunogenic epitopes. This software takes in the full-length antigen sequence as the query and is able to analyze, identify, retrieve, map and cluster of multiple classes of immunogenic epitopes, including major histocompatibility class-I, -II and B cell epitopes, with an easy-to-use graphic user interface (FIGS. 2A-C). This software provides a powerful tool to enable streamlined nanovaccine design and production (FIGS. 2D-E).

Exosome as Novel Nanocarrier

The field of exosome-based drug delivery has expanded over the past decade. Reports on loading of various cargos such as chemotherapeutics, siRNA, mRNA and proteins have firmly established that these human cell-derived nanovesicles can function as nanocarriers. Compared to existing vaccines, exosomes exhibit unique particle size (50~150 nm), favorable surface proteins that offer synergistic antigen presentation and cellular uptake abilities. Through receptor-mediated endocytosis, the default destination of exosomes is the endocytic compartment of recipient cells, resulting in effective antigen processing and presentation. This built-in feature is desirable for intracellular delivery of antigens targeted to their natural action sites, translating into better antigen presentation and driving more robust immune response. To the inventors' knowledge, a unified platform to display repetitive epitope clusters onto the surface of exosomes is a novel form of nanovaccine that has not yet been established.

Advanced Genetic Loading of Selective Epitopes

The aim of this invention was to develop an exosome-based strategy that can be used to generate epitope-displayed exosomes for driving robust B and T cell immunity. Using a genetic method to produce exosome-based vaccines is new and has a number of advantages over the existing technologies, such as soluble full-length antigen or viral-particle like vaccine. While soluble full-length antigen carries both immunogenic sequences and pathogenic domains, exosome-based vaccine carries only minimal immunogenic epitopes on "self" materials and thus are safer with reduced side effects. Additionally, endogenous membrane proteins enriched in exosomes may help to gain intracellular entry via a receptor-mediated endocytosis, a highly effective mechanism for antigen processing and presentation.

duction of safe, effective and precise vaccines (Table 1). Most of them use either whole pathogens (live attenuated and inactivated vaccines) or the full-length antigens (protein, virus-based, virus-like particle, DNA/RNA-based vaccines). Instead, our technology uses only highly selected sequences from the full-length antigens as immunogenic reagents.

TABLE 1

| Existing vaccine platforms and their pros and cons | | | |
| --- | --- | --- | --- |
| Type | Platform | Pros | Cons |
| Whole pathogen | Live attenuated | Mimic natural infection | Not suitable for immunocomprised |
| | Inactivated | Safer than live pathogen | Potential epitope alteration by inactivation |
| Full-length antigen | Protein | Established | Maybe difficult to produce |
| or subunit | Virus-based vaccine | Mimic naturally infection | More complicated manufacturing |
| | Virus-like particles | Potent response | Limited application |
| | DNA-based vaccine | Safe and well tolerated | Low immunogenicity |
| | RNA-based vaccine | Safe and well tolerated | Low temperature storage & transport |

Note:
all existing vaccine platform use either whole pathogen or the full-length antigen/subunit as immunostimulants, therefore they are pathogen/antigen-dependent, which may potentially cause tissue inflammation and organ damage.

Novel Targeted Delivery System of Antigen to Presenting Cells

By exploiting the unique features of exosomes, one can produce epitope-displayed exosomes for the targeted delivery of precise antigens to antigen presenting cells, a more efficient way for the elucidation of precise and robust immune response. Existing vaccines do not possess this unique ability and therefore are not effective in antigen presentation.

A Modular and Flexible Design Scheme

The unique features of the genetic design in this invention for producing epitope-displayed exosomes are multi-faceted. First, it enables loading of epitopes in two different locations, either at the outer surface or inside of the lumen of exosomes. While displaying at the outside will enable more epitopes, enclosed inside the lumen will protect epitopes from endogenous enzyme degrading during delivery. Second, these engineered exosomes can be monitored in live cells and in real-time via fluorescent protein reporters. Finally, this novel platform is able to provide mechanical evidence for antigen internalization, processing and presentation in cultured antigen presenting cells before moving onto animal study to confirm the safety and efficacy in animal models. Together, embodiments of this invention will be valuable for planning preclinical studies.

As stated infra the nanovaccine platform of this invention includes three key components:

(1) an integrated bioinformatics software for identification and retrieving highly immunogenic clusters from the full-length antigens;

(2) a modularly structured exosome-targeting scaffold and an streamlined assembly protocol via synthetic biology; and (3) a set of established protocols to produced exosome-based nanovaccine using surface display technology in cultured human 293T cells.

Because of the modular structure of this nanovaccine, it is possible to load antigen cargos in different places relative to the exosomal membrane. Additionally, incorporation of other functional moieties, such as reporter or adjuvant into nanovaccine are also easy to achieve. Existing vaccine platforms remain fragmented and lack coherent development strategy and streamlined methods for the rapid pro- In one embodiment, the invention can be summarized as an exosome-based method for producing a nano-vaccine. The method distinguishes inputting a full-length antigen sequence as a query in a graphic user interphase-supported software program to search online databases. The online databases are queried based on the inputted query to identify, retrieve and cluster Major Histocompatibility Class (MHC)-I epitopes, MHC-II epitopes and B-cell epitopes. Epitope clusters of the MHC-I, the MHC-II and the B-cell epitopes are then selected. The selected epitope clusters are joined and repeated to form a single linear sequence. The single linear sequence is then synthesized and subcloned into an exosome-targeting scaffold. Then the exosome-targeting scaffold is synthesized and subcloned the into a mammalian expression vector. The exosome-targeting scaffold has five distinctive domains defined as: (i) a signal peptide for directing a synthesized protein to an endoplasmic reticulum (ER), (ii) a hinge for providing flexibility of the selected epitope clusters, (iii) a transmembrane helix which dictates exosome-targeting and incorporation, together with shorter flanking sequences, (iv) an intraluminal domain for accepting a luminal cargo, and (v) a reporter for molecular tracking and imaging.

BRIEF DESCRIPTION OF THE DRAWINGS

The drawings accompanied herewith are grey scale drawings converted color drawings. For color interpretation of the grey scale drawings, the reader is referred to the priority document to which this application claims the benefit.

FIGS. 1A-C show according to an exemplary embodiment of the invention a schematic illustration of composition of traditional vaccine (FIGS. 1A-B) and the molecular method of the invention (FIG. 1C). Critical features of the molecular method include enhance safety, efficacy and precision.

(FIG. 9A) Immunization scheduling. (FIG. 9B) Assays performed on blood and tissue samples.

DETAILED DESCRIPTION

Computational Software and Antigen Analysis

Figures 1A, 1B:
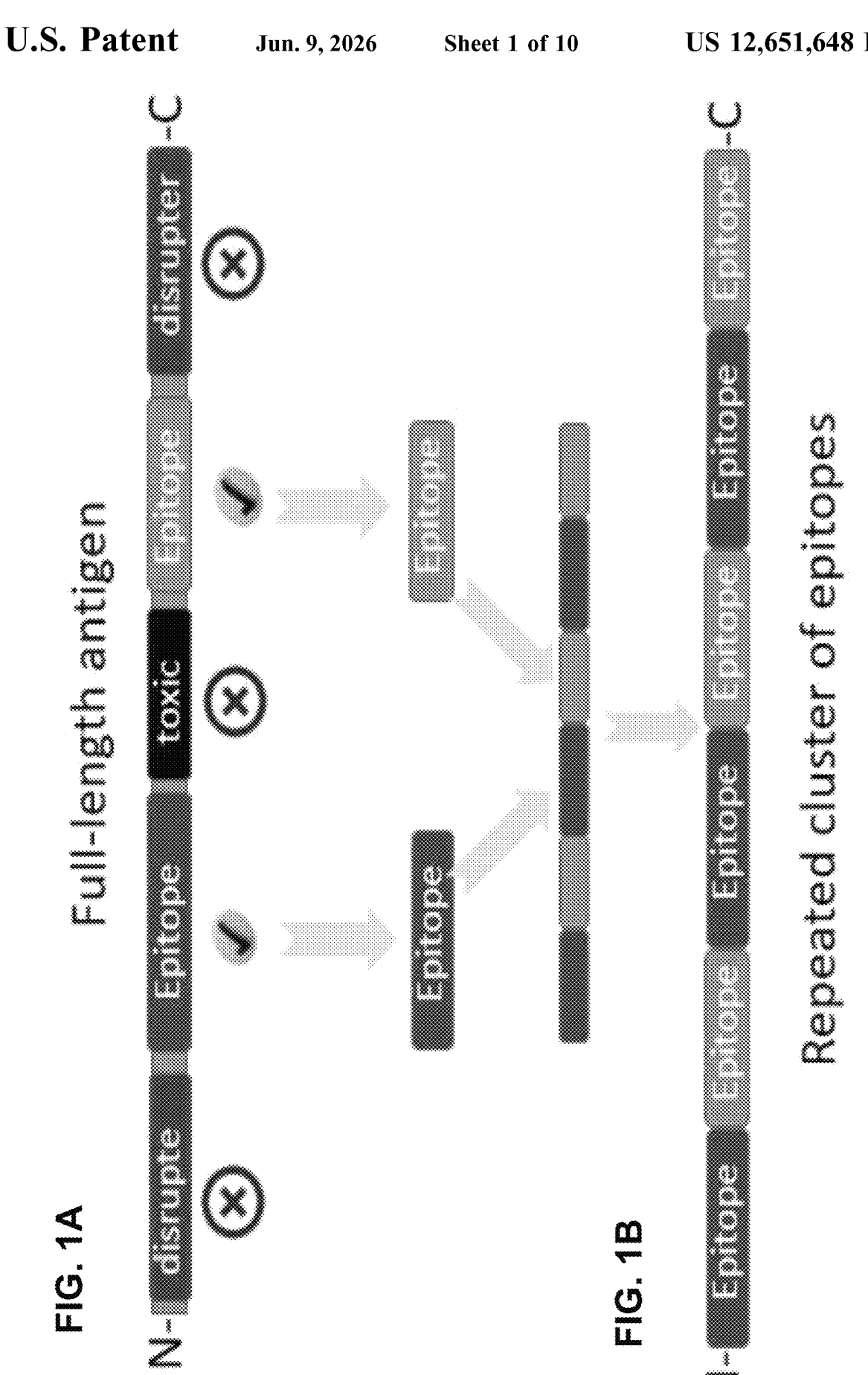
Figure 1C:
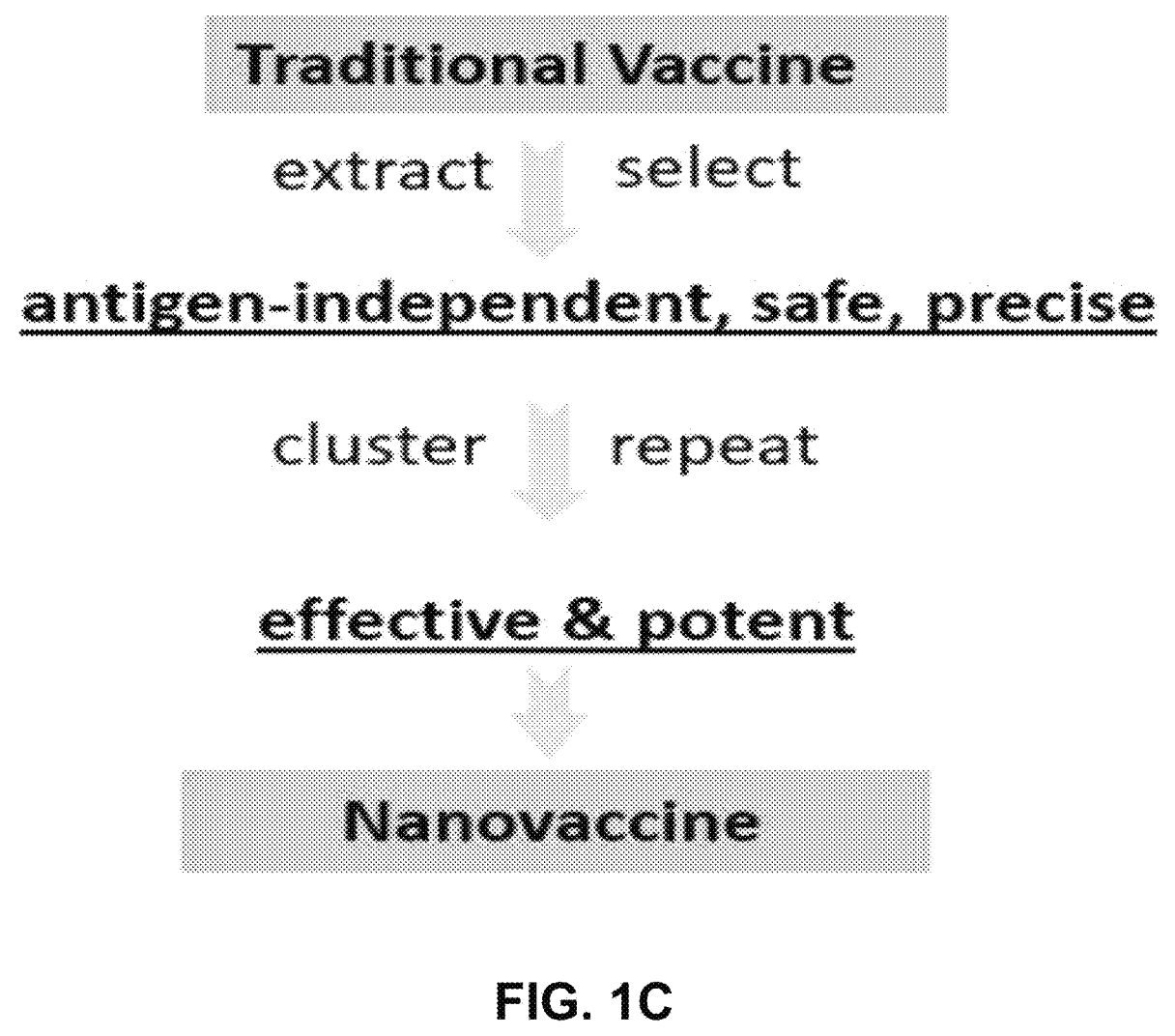
Figures 2A, 2B, 2C, 2D, 2E:
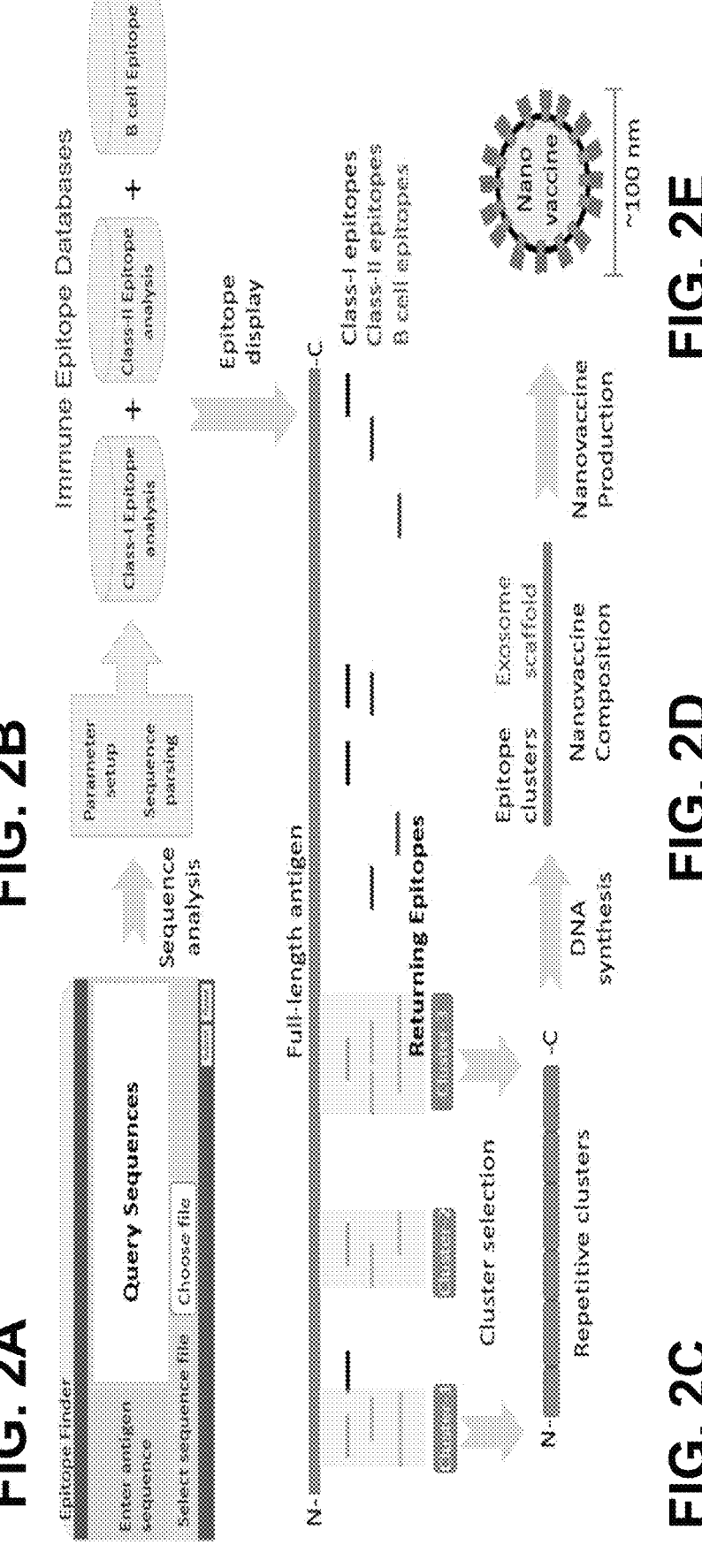
FIGS. 2A-E show according to an exemplary embodiment of the invention a schematic illustration of software functionality and workflow computer-aided design of a nano-vaccine.

The inventors have developed a computational software that can identify and retrieve all classes (MHC-1, MHC-2, and B-cell) of immunogenic epitopes embedded in sophisticated antigens originated from human viruses and cancers. When combined with synthetic biology and surface engineering technology, this software aids in streamlining the design and production of exosome-based nanovaccine (FIGS. 1A-C and FIGS. 2A-D).

Using any amino acid sequence as input, the software allows the returning of all three classes ((MHC-1, MHC-2, and B-cell) of immunogenic epitopes through parallel searching and epitope mining of multiple immunological databases. The identified epitopes include the major histocompatibility complex (MHC) MHC-1, MHC-2 and B-cell epitopes, which are essential sequences for the full activation of both T- and B-cell immunity. Reference to the software can be found, and is referenced in, U.S. Provisional Patent Application 63/397,477 filed Aug. 12, 2022, which is incorporated herein by reference.

The primary database that the software used to generate the epitopes was the Immune Epitope Database (IEDB). The query is amino-acid sequences of the chosen antigen, and the restriction of the search to specific reference alleles. The search is performed via an HTTP request using the IEDB recommended net MHC panel. This search returns data in a matrix of tab-separated values later to be stored in a data frame. The output from this request contains a list of reference alleles found on MHC-1 molecules along with a percentile rank indicating the binding affinity of that allele. The reference alleles are then filtered according to a specific threshold. Thresholds can be specified to fit user needs, but are automatically set to 0.1% percentile rank for MHC I alleles, and top 1% percentile rank for MHC II. These MHC-specific thresholds are important for the desired high immunogenicity as they ensure optimal binding affinity to the target protein sequences. The methods described above for generating highly immunogenic sequences apply to MHC-1 and MHC-2 molecules. However, different methods are necessary for acquiring domains targeted by B-cells. To search for these domains, our software defines a user agent to conduct a web search query that looks for a text area element, enters the desired protein sequence into the text area, and later finds and clicks the submit button to conduct the search. This search also returns a matrix of tab-separated values containing percentile ranking, which are later used to find highly immunogenic sites targeted by B-cells. Once all immunogenic sequences have been isolated, they are returned as an output in three different colors, each corresponding to the various domains targeted: MHC-1 (in red), MHC-2 (in blue), and B-cell (in purple) epitopes (reader is referred to the U.S. Provisional Patent Application 63/397, 477 filed Aug. 12, 2022, which is incorporated herein by reference, for interpretation of the colors). These are presented alongside two black texts representing the sequence inputted by the user to provide visual reference of the location of the immunogenic sequences.

Figure 3:
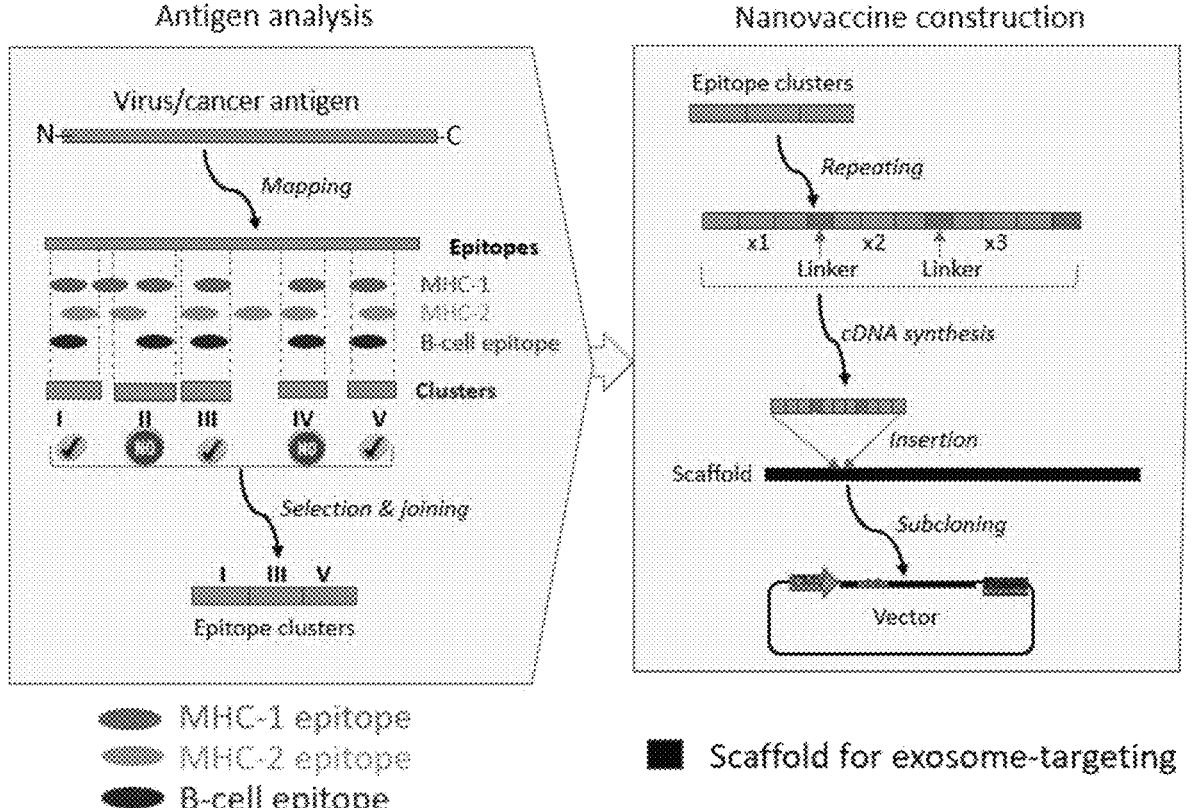
FIG. 3 shows according to an exemplary embodiment of the invention an assembly of epitope clusters into exosome-targeting scaffold. Antigen analysis allows the identification, mapping and finally selection of highly immunogenic clusters from the full-length antigen (right panel). The selected epitopes are joined together via linker sequences and subsequently inserted into the preassembled exosome-targeting scaffold in pcDNA3.1 vector (left panel).

In U.S. Provisional Patent Application 63/397,477 filed Aug. 12, 2022, which is incorporated herein by reference, FIG. 3 shows the output screen shot for the identification and mapping of 3 classes of epitopes, including MHC-1 (in red), MHC-2 (in blue), and B-cell (in purple) epitopes, in a cancer related antigen (alpha-fetoprotein, AFP).

Assembling of Epitope Clusters into Exosome-Targeting Scaffold

Assembly Strategy

Antigen analysis using the computational software presented herein will yield multiple epitope clusters (>=5 clusters) as shown in FIG. 3 (right panel). Typically, 3 clusters in a given antigen are selected in considering of their location, function and accessibility in the full-length antigen. The selected clusters are then joined together to form a single linear sequences such as cluster I-II-V. To enhance their immunogenic strength, epitope clusters are repeated for 3 times and a flexible linker (GGGGGS) is included. The complementary coding sequences of the 3× epitope-cluster-linker are chemically synthesized and subcloned into exosome-targeting scaffold as shown in FIG. 3 (left panel).

Exosome-Targeting Scaffold

The exosome-targeting scaffold is composed of 5 distinctive domains:

1) a signal peptide, directing the synthesized protein to endoplasmic reticulum (ER);
2) a hinge, providing flexibility of displayed epitope clusters;
3) a transmembrane helix with flanking sequences;

4) a short intraluminal domain to accept additional luminal cargo; and 5) a reporter such as green fluorescence protein for molecular tracking and imaging.

Table 2 summarizes the components of exosome-targeting scaffolds and their functions.

Cell Culture

The engineered human kidney 293T cells were passaged 2-3 times each week. Depending on the experimental design and assay, transfection was normally conducted on 6-well plate or 3.5 cm dish in 2 mL/well medium of DMEM (Gibco Dulbecco's Modified Eagle Medium) supplemented with

TABLE 2

Components of exosome-targeting scaffold

| Name of component | Origin | Function |
|---|---|---|
| Signal peptide | Gaussian luciferase | Translocate protein to ER membrane |
| Hinge sequence | Human CD8 | Provide extension and flexibility of displayed epitopes |
| Transmembrane helix (TM) | Viral envelope protein (VSVG) | Translocate protein to exosome and provide membrane Anchoring |
| Intraluminal domain | Viral envelope protein | Provide flexibility of intraluminal reporter |
| Imaging reporter | Green fluorescent protein | Provide a means of imaging and trafficking |

Abbreviations: Vesicular stomatitis virus envelop glycoprotein (VSVG); Transmembrane helix (TM).

Figure 4:
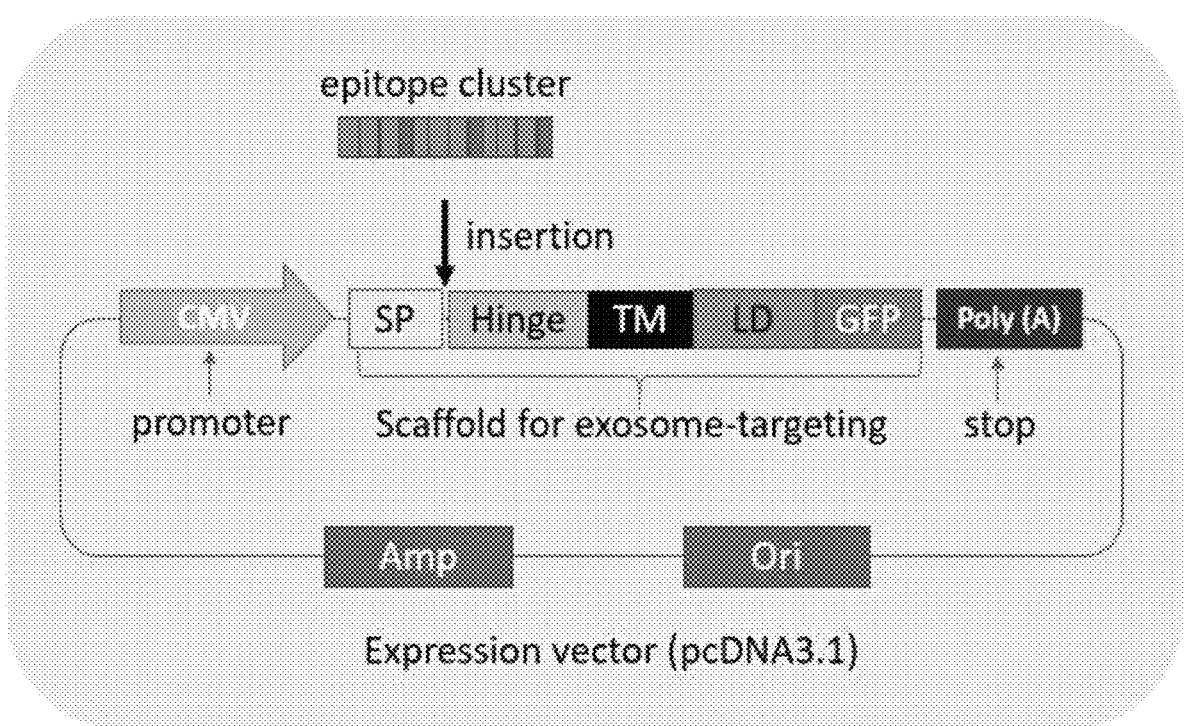
FIG. 4 shows according to an exemplary embodiment of the invention construction of exosome-targeting scaffold in mammalian expression vector. The pcDNA vector provides a mammalian CMV promoter and a transcription stop signal Poly (A) to ensure high level of expression of exosome-targeting scaffold. The sequences of the epitope cluster is inserted between the SP and Hinge inside the scaffold.

The complementary DNA of exosome-targeting scaffold is synthesized and subcloned into a mammalian expression vector (pcDNA3.1) through a service by Genscript (Piscataway, NJ, USA). This expression serves as an acceptor construct for accommodating the 3× epitope with the linker sequences as illustrated in FIG. 4.

Construction of Nanovaccine Expression Vector

Figure 5:
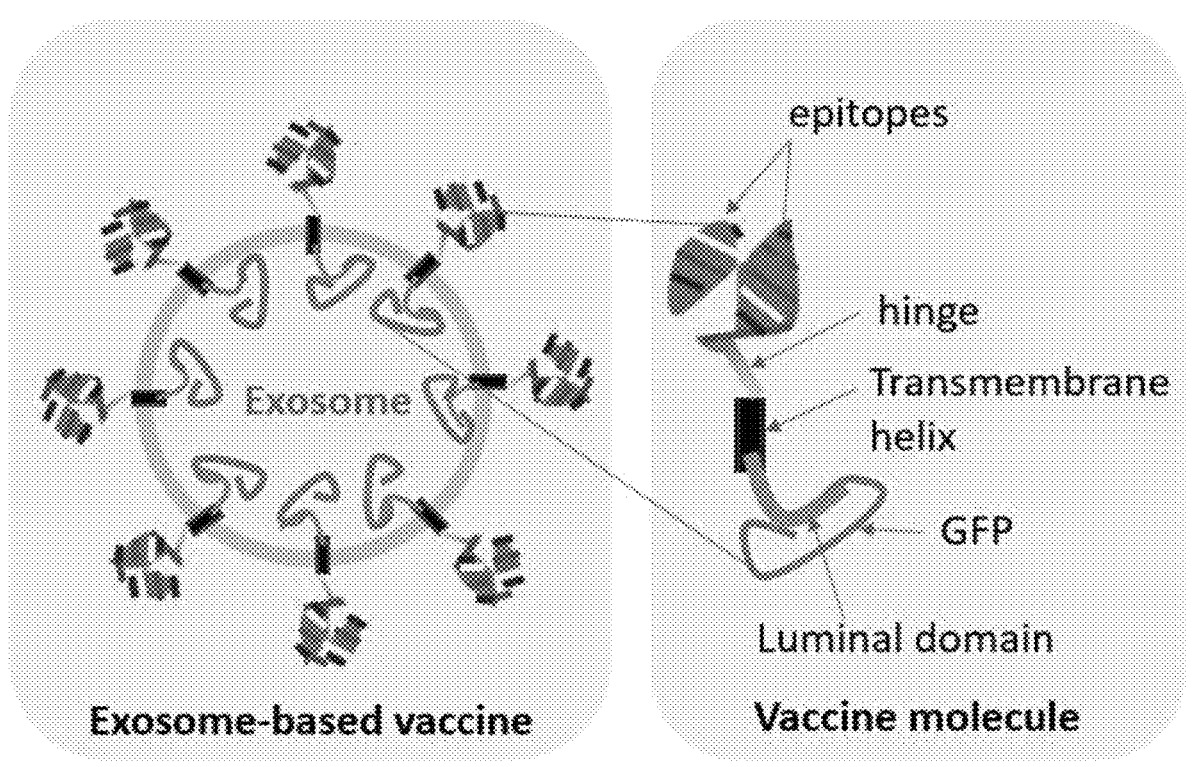
FIG. 5 shows according to an exemplary embodiment of the invention a structure of engineered exosome-based vaccine. Epitopes are displayed on the outer surface, while the imaging molecule of GFPare loaded in the lumen of exosomes via exosome-targeting scaffold (Left panel). The domain structure of rational designed vaccine molecule (Right panel).

Expression is constructed by synthesis and insertion of the 3× epitope clusters-linker sequences into exosome-targeting scaffold inpcDNA3.1 (Thermo Fisher Scientific). Specifically, the synthesized double-stranded DNA is subcloned into pre-synthesized exosome-targeting scaffold between the signal peptide and the hinge as shown in FIG. 5.

This construct produces a transmembrane protein on the surface of exosomes with the epitope clusters projected from the outer surface of exosomes following transfection into cultured mammalian cells. FIG. 5 illustrates the epitope clusters displayed on the surface of engineered exosomes.

Nanovaccine Production, Preparation and Characterization

Cells and Reagents

Human embryonic kidney cells (293T) were purchased from Alsterm (Richmond, CA). High glucose DMEM, Opti-MEM medium, and fetal bovine serum were purchased from Thermo Fisher Scientific (Waltham, MA). Chemical defined and serum-free (UltraCulture medium) was purchased from Lonza (Prtsmouth, NH). Transfection reagent polyethylenimine (PEI) were from Sigma-Aldrich (St. Louis, MO). Lipofectamine2000 from Invitrogen, and FuGene6 from Promega (Madison, WI). Nuclear staining solution Hoechst 33342 was purchased from ThermoFisher Scientific (Fremont, CA). EV precipitation solution (ExoQuick-TC) was obtained from System Biosciences (Palo Alto, CA).

Vectors and Fusion Genes

Scaffolds, including Gaussian luciferase signal peptide, the human CD8 hinge and vesicular stomatitis virus glycoprotein (VSVG) transmembrane helix with its flanking sequences and luminal domain, were fused with enhanced GFP at the C-terminus of all scaffolds as reported previously (doi: 10.2147/IJN.S133430. eCollection 2017). All expression vectors were constructed similarly. The open reading frame of the exosome-targeting scaffold was typically generated by synthesis and cloned in frame with the GFP reporter following the cytomegalovirus promoter (CMV). All final constructs were verified by double stranded DNA sequencing to ensure fidelity.

10% FBS (fetal bovine serum) and 1% Pen Strep (Gibco Penicillin Streptomycin, 10,000 units/ml).

Transfection

A day before transfection, each Imaging dish (Cellvis 4-well Glass 35 mm Bottom Dish with 20 mm well) was prepared with 5004, of DMEM+10% FBS+1% Pen Strep media, and 124, of cells, and allowed to incubate overnight. The next day, a confluency threshold of 40-50% was confirmed to ensure quality of transfection. To prepare the transfection reagent for each well of cells, 254, of OPTIMEM (GibcoOpti-MEM 1× Reduced Serum Media) with 1% Pen-Strep was added into two separate 1.5 mL microcentrifuge tubes. While 2.5 μL of PEI was added to tube No. 1, 0.5 μg of our construct's DNA was added to the tube No. 2. Following the combination of the content of these two tubes, let rest at room temperature for 20 minutes to allow PEI to form around the DNA. The entire contents of the combined tube, ~53 μL, was then added dropwise to a single well of the glass bottom plate. The imaging plates were then returned to the incubator and imaged daily at 24, 48 and 72 hours.

Fluorescence and Confocal Microscopy

Figure 6:
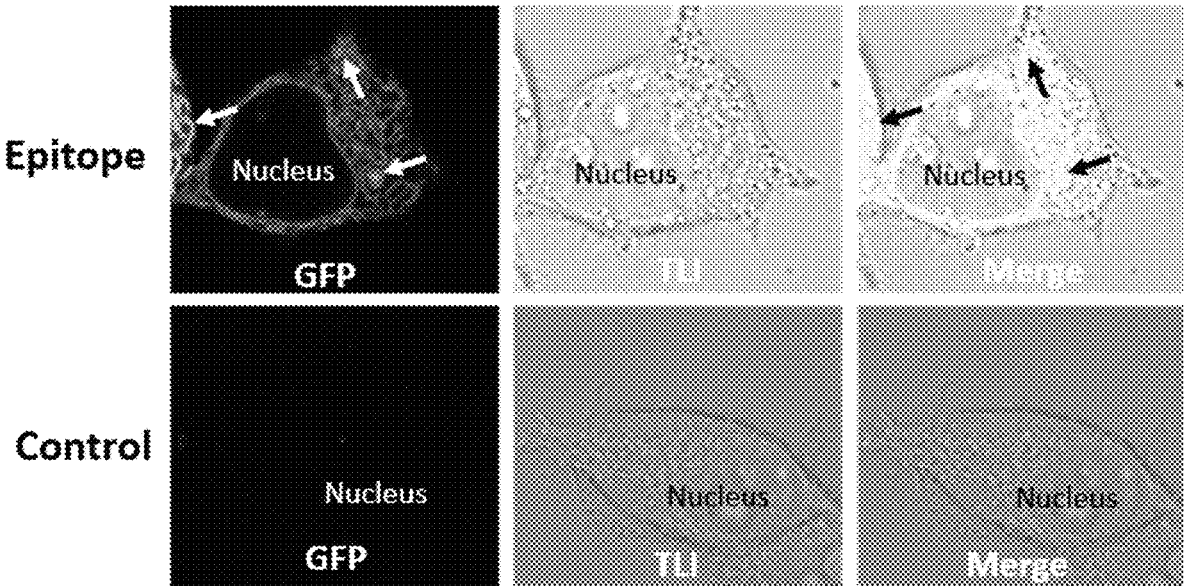
FIG. 6 shows according to an exemplary embodiment of the invention expression of nano-vaccine constructs in human 293T cell. Images were taken 48 hours after transfection to show successful expression of nano-vaccine in transfected (upper panels) vs. non transfected controls (lower panels). Arrows indicate GFP in exosomes/membranes.

Images of cultured live cells or fluorescently labeled exosomes were recorded using Leica TCS SP8 confocal microscope (FIG. 6). To demonstrate intracellular localization of the genetically produced nanovaccines, both fluorescence and light transmitted images from the same filed were recorded and merged (FIG. 6). Image adjustments such as brightness and contrast were applied to the entire image frame using instrument software.

Production of Engineered Exosomes

To prepare modified exosomes, a 150 mm tissue culture plate was used for each sample with 15 mL of DMEM (Gibco Dulbecco's Modified Eagle Medium)+10% FBS+ 1% Pen Strep. 350 ul of cells was then added to each plate and were incubated until reaching 70-80% confluency after ~3 days. Subsequently, each plate was transfected by 2 ml preparation containing 20 μg of DNA, 100 μL of PEI, each diluted in 1 mL of OPTIMEM. The combined DNA and PEI was allowed to rest for 20 minutes before adding into the 150 mm plate. Cells were then incubated for additional 24 hours, followed by replacing with 15 mL of UltraCULTURE (LonzaUltraCULTURE Serum Free Cell Culture Media) media to allow exosome production and accumulation in the conditioned medium for another 72 hours.

Engineered exosomes were isolated from conditioned Preparation of Engineered Exosomes medium by a combination of ultrafiltration, precipitation and centrifugation. After the 72-hour incubation in UltraCULTURE, the culture media was removed from the plates and collected in 50 mL tubes. The 50 mL tubes containing culture media were then centrifuged at 1500 g for 10 minutes in a tabletop centrifuge. The cell culture media was then syringe filtered using 30 mL syringes (BD 30 mL Syringe Luer-Lok Tip) and 0.2 μm syringe filters (VWR Sterile Syringe Filter w/ 0.2 Polyethersulfone Membrane) into a new 50 mL tube. 5 mL of Exo-Quick TC (SBI Exo-Quick TC for tissue culture media) was then added to each tube and the tubes were stored in the refrigerator overnight. The next day, the Exo-Quick and media solution was centrifuged at 3000 g for 1.5 hours in a tabletop centrifuge. The supernatant was then removed from the tubes and the tubes were placed upside down to dry for 10 minutes. Once the tubes were dry, the exosome pellets were each re-suspended in 2004, PBS and stored at −20 degrees Celsius for future use.

Nanoparticle Tracking Analysis

Figure 7A:
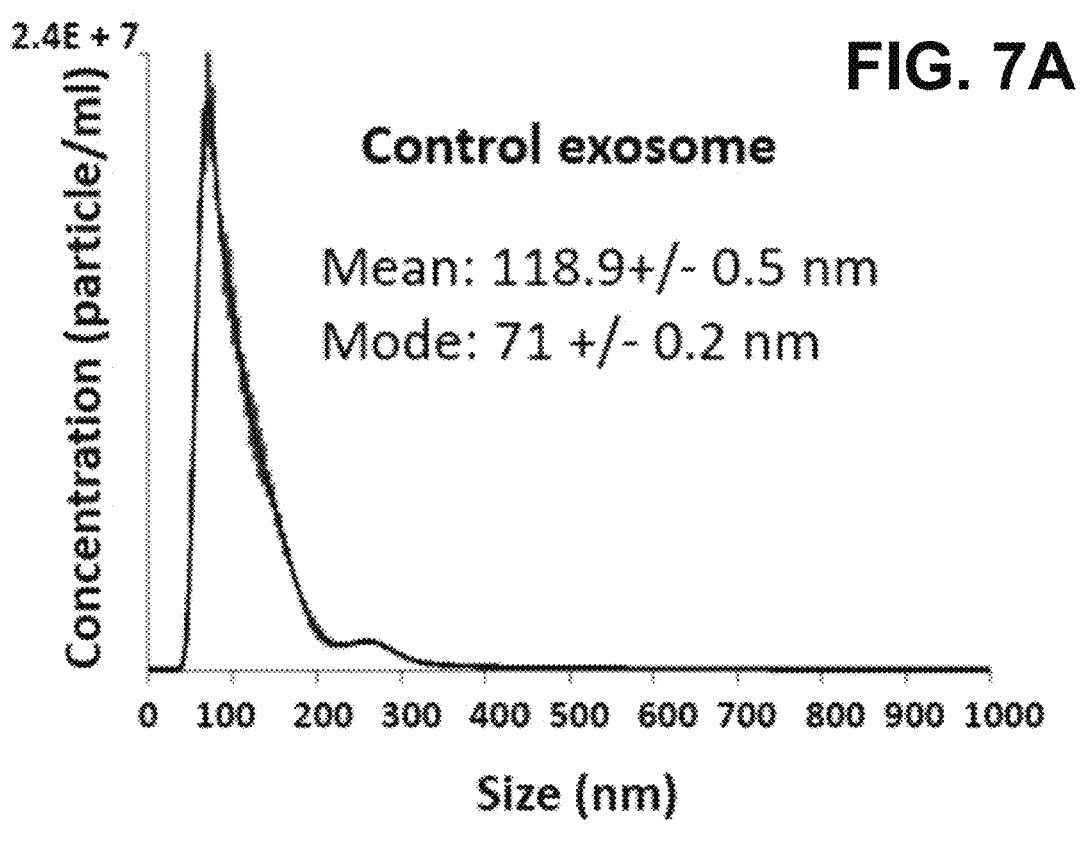
FIGS. 7A-B show according to an exemplary embodiment of the invention nanoparticle tracking analysis (NTA). NTA profiles the control (FIG. 7A) or epitope-displayed (FIG. 7A) exosomes isolated from conditioned medium of 293T producer cells at 3 days post-transfection. The graphs are the result of finite track length assessment. Red bar indicates +/−one standard error of mean in triplicate.
Figure 7B:
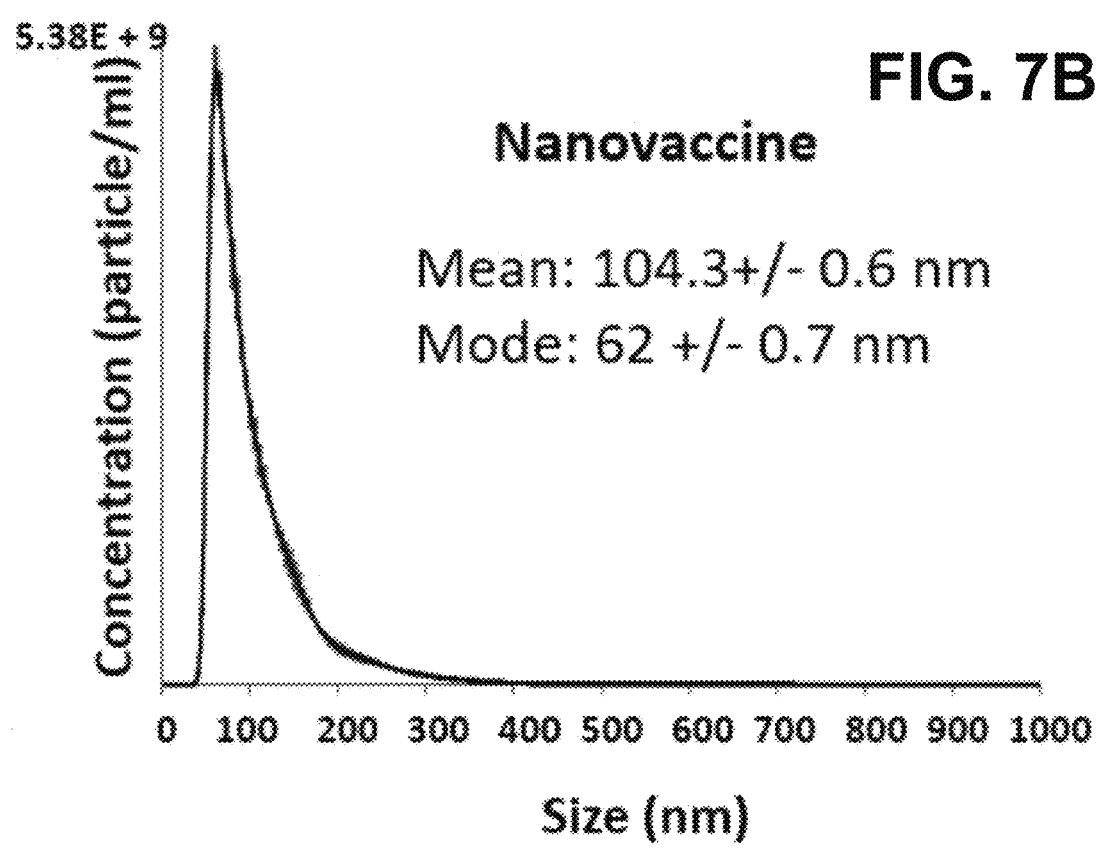

Nanoparticle tracking analysis was conducted using a NanoSoght LM10 instrument with a 405 nm and 60 mV laser sources. Typically, 1 mL of a diluted exosome samples was subjected to laser light scattering and Brownian motion of particles were recorded and analyzed for sizing. Size distribution of exosomes were calculated and graphed by the NTA software. NTA was used to characterize the particle concentration, size and size distribution of each preparation. NTA analysis of exosomes demonstrates that a single peak of vesicle population with a mode of 62+/−0.7 nm for 3× epitope displayed exosomes, similar to those of non-modified controls (71+/−0.6 nm) (FIGS. 7A-B).

Confocal Imaging of the Engineered Exosomes

Figures 8A, 8B:
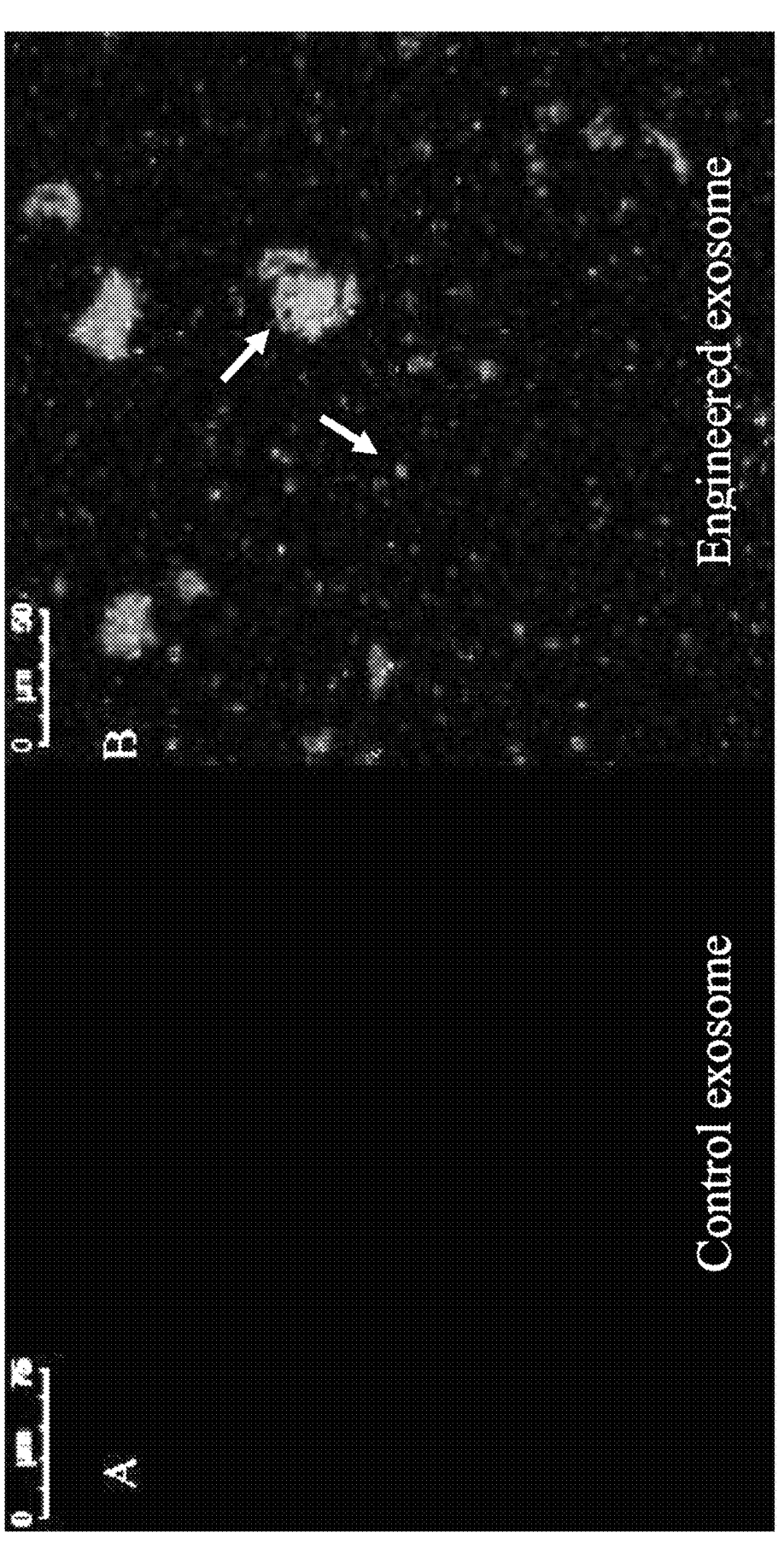
FIGS. 8A-B show according to an exemplary embodiment of the invention confocal and fluorescence image of engineered exosomes form the controls (FIG. 8A) and successfully epitope-displayed exosomes (FIG. 8B). Arrows indicate individual/clustered exosomes. Scale bar, 50 μm.

For each exosome sample, 3~10 μL of exosomes in PBS were added onto a 35 mm imaging plate to be imaged with the confocal microscope. An overview image of each plate was taken at 1×zoom and the GFP gain threshold was lowered to 22 to facilitate a better overview of exosome fluorescence. FIG. 8. Shows the successfully engineered exosomes (GFP positive), while native exosomes are GFP negative.

Safety and Effectiveness of Nanovaccine Using Experimental Animals

Figures 9A, 9B:
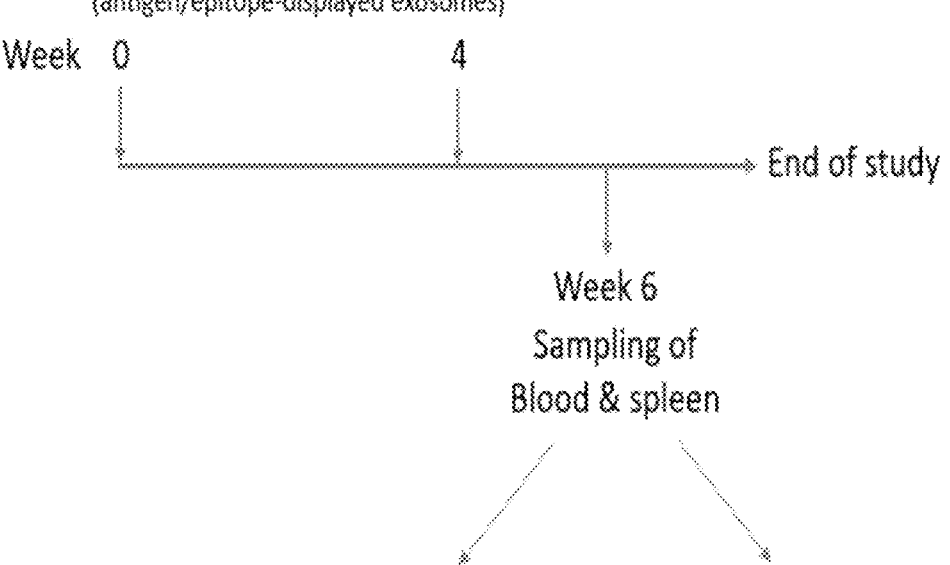
FIGS. 9A-B show according to an exemplary embodiment of the invention effects of exosome-based nano-vaccine on the production of antigen-specific B and T cell responses in BALB/c mice.

A mouse model was used to evaluate the safety and effectiveness of exosome-based vaccines. Specifically, immune responses of both antibody (Spike-specific IgG and IgA responses) and cell-mediated response (quantification of Th-associated cytokine production from specific antigen restimulated splenocytes) can be quantified using commercial assay kits (FIGS. 9A-B). These assays determine whether nano-vaccines can induce robust humoral and cellular immune responses. During the immunization, mouse body weight can be measured weekly and any adverse symptoms and/or death events can also be monitored daily for the evaluation of vaccine safety.

Mice and Vaccination

BALB/c mice (6-8 weeks old) can be used in the vaccination study. Mice can be injected i.m. with 50 μg unmodified EVs purified from untransfected 293T or CHO cells or 50 epitope-displayed EVs via transfection. All immunizations can be performed twice in 4-week intervals. Blood samples (150 μl/mouse) can be taken at week 4 and 6, and mice can be sacrificed at week 6. For B-cell response, spike-specific IgG and IgA are semi-quantified by ELISA using a service from Genscript. For T-cell response, splenocytes are prepared from sacrificed mice at week 6 as reported[11]. PBS-washed splenotyes are cultured with 10 ug/ml recombinant spike proteins (Gencript) and 5 μg/ml Con A (experiment group) or medium (control group) for 7 days at 37° C. Following incubation, cell culture supernatants are harvested and antigen-stimulated Th-related cytokines are measured by a Mouse ProcartPlex Panel (Invitrogen ThermoFisher Scientific) on a BioPlex 200 (Bio-Rad) platform, according to the manufacturer's instruction. Symptom and body weight are monitored and measured once a week until the week 6.

What is claimed is:

1. An exosome-based method for producing a nanovaccine, comprising:
   (a) inputting a full-length antigen sequence as a query in a graphic user interphase-supported software program to search online databases;
   (b) querying the online databases based on the inputted query to identify, retrieve and cluster Major Histocompatibility Class (MHC)-I epitopes, MHC-II epitopes and B-cell epitopes;
   (c) selecting epitope clusters of the MHC-I, the MHC-II and the B-cell epitopes;
   (d) joining and repeating the selected epitope clusters to form a single linear sequence;
   (e) synthesizing and subcloning the single linear sequence into an exosome-targeting scaffold, wherein the exosome-targeting scaffold has five distinctive domains defined as:
      (i) a signal peptide for directing a synthesized protein to an endoplasmic reticulum (ER);
      (ii) a hinge for providing flexibility of the selected epitope clusters;
      iii) a transmembrane helix which dictates exosome-targeting and incorporation, together with shorter flanking sequences;
      (iv) an intraluminal domain for accepting a luminal cargo; and
      (v) a reporter for molecular tracking and imaging; and
   (f) synthesizing and subcloning the exosome-targeting scaffold into a mammalian expression vector.

* * * * *